United States Patent [19]

Weber et al.

[11] Patent Number: 4,885,383

[45] Date of Patent: Dec. 5, 1989

[54] PROCESS FOR THE PREPARATION OF CARBOXYLIC ACID METHYL ESTERS

[75] Inventors: Jurgen Weber; Helmut Springer, both of Oberhausen; Peter Lappe, Dinslaken, all of Fed. Rep. of Germany

[73] Assignee: Hoeschst Aktiengesellschaft, Fed. Rep. of Germany

[21] Appl. No.: 248,544

[22] Filed: Sep. 23, 1988

[30] Foreign Application Priority Data

Sep. 30, 1987 [DE] Fed. Rep. of Germany ....... 3732995

[51] Int. Cl.$^4$ .............................................. C07C 67/03
[52] U.S. Cl. ..................... 560/103; 560/98; 560/100; 560/101; 560/102; 560/105; 560/204; 560/231; 560/265
[58] Field of Search ................. 560/98, 100, 101, 102, 560/103, 105, 204, 231, 265

[56] References Cited

FOREIGN PATENT DOCUMENTS 2050678 4/1972 Fed. Rep. of Germany .

OTHER PUBLICATIONS

J. Org. Chem., 24,261, (1959).
Clinton et al., J. Amer. Chemi. Soc., 70,3135, (1948).
Harrison et al., Chemistry and Industry, p. 1568, (1968).

*Primary Examiner*—Vera C. Clarke
*Attorney, Agent, or Firm*—Jordan B. Bierman

[57] ABSTRACT

A process for the preparation of methyl carboxylates by the reaction of mono or dicarboxylic acids having more than 5 carbon atoms and methanol in the presence of acidic catalysts at temperatures from 100° to 150° C. and below the boiling point of the carboxylates being produced.

13 Claims, No Drawings

PROCESS FOR THE PREPARATION OF CARBOXYLIC ACID METHYL ESTERS

The invention relates to a process for the preparation of methyl esters of carboxylic acids having more than 5 carbon atoms in the molecule by reacting them with methanol. The reaction takes place in the presence of a catalyst at temperatures which are 100° C. or more but below the boiling point of the resultant ester.

BACKGROUND OF THE INVENTION

The most common process for the preparation of carboxylic acid esters is the direct reaction of the acids with alcohols. It leads to an equilibrium in which alcohol, acid, ester and water are all present. The adjustment of the equilibrium is affected by catalysts.

This procedure is generally economic only when the esterification equilibrium is shifted as far as possible towards the formation of esters. Suitable measures of achieving this aim are the use of a high excess of one of the starting materials or the removal of one of the products from the reaction mixture. Normally, the alcohol is added in excess, or the reaction water or the ester is removed from the reaction mixture.

The reaction water can, for example, be separated by the addition of a dehydrating agent (which binds the water), or preferably by azeotropic distillation with the aid of separating agents. With the extractive esterification process, the ester formed is selectively dissolved out of the reaction mixture with the aid of a solvent.

However, the removal of the reaction water by azeotropic distillation is not suitable for the preparation of methyl esters of carboxylic acids, since methanol distills with the separating agent in such amounts that no phase separation takes place.

According to a process described in J. Org. Chem. 24, 261 (1959), methyl esters of carboxylic acid are obtained by the reaction of carboxylic acids with methanol in the presence of acetone dimethyl acetal, the dimethyl acetal acting as a hydrophilic agent and supplier of methanol. If adipic acid, methanol and acetone dimethyl acetal are reacted in a molar ratio of 4:5:8, a 94% yield of dimethyladipate is obtained. The economy of this procedure is impaired by the fact that the use of acetone dimethyl acetal increases the raw material costs, and the formation of acetone during the course of the reaction increases the amount of distillation required.

According to the process of Clinton and Laskowski (J. Amer. Chem. Soc. 70, 3135 (1948)), in order to prepare methyl esters, a carboxylic acid and methanol are heated under reflux in the presence of sulfuric acid as a catalyst and methylene or ethylene chloride without the reaction water being removed. Then the organic phase containing the ester is separated and recovered. This procedure not only requires the use of chlorinated hydrocarbons as solvents for the ester, but also necessitates long reaction periods of 6 to 15 hours.

DE-OS No. 20 50 678 describes the preparation of esters for carboxylic acids and alcohols in the presence of inert organic solvents and esterification catalysts. Hydrocarbons having a boiling point of −10° to 200° C. are used as the solvents, and acids—or materials forming acids in the aqueous medium—are used as catalysts together with aqueous saline solutions. According to the examples, the preparation of methyl esters of saturated carboxylic acids requires reaction periods of 10 hours (propionic acid) to 60 hours (valeric acid), the ester yields being only 68% and 66%, respectively. The long reaction periods, the use of hydrocarbons as extraction agents, ant the unsatisfactory speak against the use of this process variant.

Other processes for obtaining methyl carboxylates were developed more for use in the laboratory than for use on an industrial scale. This includes esterification with diazo methane or with $BF_3$-methanol reagent. The use of molecular sieves (Harrison et al., Chemistry and Industry (1968), page 1568) for adsorbing the reaction water has not been adopted on an industrial scale.

DESCRIPTION OF THE INVENTION

The purpose of invention was to avoid the foregoing disadvantages of the state of the art and to develop a generally applicable process for the preparation of methyl esters of higher carboxylic acids which, under simple reaction conditions, permits the economic recovery of high yields of pure compounds.

These results are achieved by a process for the preparation of such esters by the reaction of saturated or unsaturated, straight or branched chain, mono or dicarboxylic acids having more than 5 carbon atoms in the molecule with excess methanol in the presence of an acid catalyst. It is characterized in that the methanol is added to a mixture of carboxylic acid and catalyst at temperatures of 100° to 150° C., but below the boiling point of the resultant ester, about 1 to about 6 mols of methanol being used per equivalent of carboxylic acid.

Although the reaction temperature is appreciably above the boiling point of methanol, the process according to the invention surprisingly permits very high yields of methyl carboxylate to be prepared easily in a simple manner and with a limited excess of methanol. Owing to the low boiling point of methanol, it was to be expected that the alcohol would be removed from the reaction mixture in such large amounts that only partial conversion would be achieved and most of the carboxylic acid would be recovered unchanged.

According to the claimed process, straight or branched chain, saturated or unsaturated, aliphatic, araliphatic or aromatic, mono or dicarboxylic acids having more than 5 carbon atoms can be used as starting materials. Examples of such acids are heptanoic acid, dipropylacetic acid, 2-ethylhexanoic acid, cyclohexanoic acid, 2-hexenoic acid, adipic acid, phenylacetic acid, benzoic acid. The carboxylic acids can either be used as uniform compounds or in the form of mixtures of two or more acids.

Strong mono or multibasic, non volatile inorganic or organic acids, such as sulfuric acid, phosphoric acid, methane sulfonic acid, ethane sulfonic acid, chlorosulfonic acids, and p-toluene sulfonic acid are particularly useful as esterification catalysts, but acid salts such as sodium hydrogen sulfate can also be used. Concentrated sulfuric acid has proven particularly suitable.

A feature of the invention is carrying out the reaction at temperatures of 100° C. or more, but below the boiling point of the ester formed. Temperatures of between 100° and 150° have proved suitable. It is appropriate to work at temperatures of 110° to 130° and in particular 115° to 125° C.

Methanol is used in excess. About 1 to about 6 mols of methanol are used per equivalent of carboxylic acid. Preferably 2.0 to 5.0, and in particular about 3.0 to 4.0, mols of methanol are reacted with an equivalent of carboxylic acid. 0.1 to 3, in particular 0.5 to 1.5, grams of concentrated sulfuric acid, which is particularly suitable as a catalyst, are added per mole of carboxylic acid.

In order to put the new procedure into practice, carboxylic acid and the catalyst are placed in a reactor and methanol is added continuously through a feed line while the mixture is stirred. Under the conditions of the claimed process, primarily water and methanol and, in addition, small amounts of the ester formed continuously, distill out of the mixture. Most of the ester remains in the reactor. If the reaction is conducted batchwise, the mixture is removed from the reactor at the end of the reaction. If the reaction is conducted continuously, the reaction mixture containing the product is continuously removed from the reactor, but it is carefully ensured that a constant liquid volume is maintained in the reactor. With this procedure, not only methanol must be added to the reactor, but also supplementary amounts of carboxylic acid and catalyst to replace those which are removed with the reaction product. these three components can be supplied separately, but preferably as a mixture. The reaction product is liberated from the catalyst in known manner by washing with water and then recovered by distillation. Further amounts of ester can also be recovered from the distillate which consists mainly of water and methanol.

The yields of the desired methyl ester of carboxylic acid are very high. With discontinuous or batch type reactions, they are mostly over 95% of the theoretical value, based on the acid used. The products obtained according to the claimed process are colorless and contain more than 99% carboxylic acid methyl ester.

The following examples illustrate, but do not limit, the scope of this invention.

EXAMPLE 1

Preparation of n-Heptanoic Acid Methyl Ester 390.6 of n-heptanoic acid (3.0 mols) and 3.0 g of concentrated sulfuric acid are placed in a 1-liter flask equipped with a stirrer, internal thermometer, feed tube, and a 12 cm Vigreux column with a Claisen bridge and heated to 125° C. With the aid of a pump, a total of 384.0 g of methanol (12.0 mols) is added through the feed dip tube over a period of 6 hours. With a head temperature of 66° to 86° C., 393.5 g of distillate are formed within this period. The residue is washed with water at about 40° C. to separate the catalyst. 380.5 g remain. The distillate and residue have the following composition:

|  | Distillate (%) | Residue (%) |
|---|---|---|
| Water | 13.60 | 0.02 |
| Methanol | 70.80 | 2.53 |
| Methyl ester | 15.35 | 97.23 |
| n-heptanoic acid | 0.12 | — |
| Miscellaneous | 0.13 | 0.22 |

The yield of n-heptanoic acid methyl ester is 99.4% of the theoretical value based on the n-heptanoic acid used.

EXAMPLE 2

Continuous Preparation of 2-Ethylhexanoic Acid Methyl Ester 173.0 g of a feed mixture consisting of 598.4 g of 2-ethyl-hexanoic acid, 397.8 g of methanol, and 3.8 g of concentrated sulfuric acid is placed in a 1-liter flask equipped with a bottom valve, a stirrer, an internal thermometer, and a Claisen bridge including a receiver. The flask contents are stirred for 30 minutes at 120° C. and the distilled amounts are collected in the receiver. While a temperature of 120° C. is maintained, the feed mixture is added continuously to the flask in an amount sufficient to maintain a constant reactor volume of 300 to 320 ml, allowing for the distilled amounts and amounts drawn off through the bottom valve. After the system has been adjusted to equilibrium, the following balance is obtained with a test period of 6 hours:

| Head temperature (°C.) | | 71–74 |
|---|---|---|
| Bottom temperature (°C.) | | 120 |
| Reactor contents (ml) | | 300–320 |
| Space velocity | $\frac{V}{V \times hr}$ | 1.26–1.34 |
| Feed (g) | | 2075.4 |
| Distillate (g) | | 859.8 |
| Residue (g) (drawn off) | | 1215.6 |

The distillate and draw-off residue (after washing) have the following compositions:

|  | Distillate (%) | Residue drawn off (%) |
|---|---|---|
| Methyl ester | 13.70 | 65.10 |
| 2-Ethylhexanoic acid | — | 31.45 |
| Methanol | 73.88 | 0.03 |
| Water | 12.30 | 1.50 |
| Rest | 0.12 | 1.92 |

EXAMPLE 3

Preparation of Dipropylacetic Acid Methyl Ester

The reaction is performed and the catalyst separated in the same manner as described in Example 1.
Acid feed: 432.6 g dipropylacetic acid (3.0 mols)
Catalyst: 3.0 g concentrated H₂SO₄
Test duration: 6 hours
Methanol added: 64.0 g/hr. (2.0 mols)
Bottom temperature: 125° C.
Head temperature: 69°–81° C.
Amount of distillate: 401.4 g
Residue: 414.6 g (catalyst-free)
Product composition:

|  | Distillate (%) | Residue (%) |
|---|---|---|
| Water | 12.90 | 0.11 |
| Methanol | 70.70 | 1.76 |
| Methyl Ester | 15.07 | 96.00 |
| Dipropylacetic acid | 1.20 | 2.00 |
| Miscellaneous | 0.12 | 0.13 |

The yield of methyl dipropylacetate is 96.6% of the theoretical value, based on the dipropylacetic acid used.

EXAMPLE 4

Preparation of Cyclohexane Carboxylic Acid Methyl Ester

The reaction is performed and the catalyst separated as described in Example 1.

Acid feed: 384.6 g cyclohexane carboxylic acid (3.0 mols)
Catalyst: 3.0 g concentrated $H_2SO_4$
Test duration: 6 hours
Methanol added: 64.0 g/hr. (2.0 mols)
Bottom temperature: 125° C.
Head temperature: 67°–85° C.
Amount of distillate: 367.6 g
Residue: 401.0 g (catalyst-free)
  Product composition:

|  | Distillate (%) | Residue (%) |
| --- | --- | --- |
| Water | 13.65 | 0.12 |
| Methanol | 76.22 | 2.83 |
| Methyl ester | 9.40 | 95.92 |
| Cyclohexane Carboxylic acid | 0.22 | 0.33 |
| Miscellaneous | 0.51 | 0.74 |

The yield of cyclohexane carboxylic acid methylester is 98.2% of the theoretical value, based on the cyclohexane carboxylic acid.

EXAMPLE 5

Preparation of 2-Hexenoic Acid Methyl Ester

The reaction is performed and the catalyst separated in the manner described in Example 1.
Acid feed: 342.6 g 2-hexenoic acid (3.0 mols)
Catalyst: 3.0 g concentrated $H_2SO_4$
Test duration: 6 hours
Methanol added: 64.0 g/hr. (2.0 mols)
Bottom temperature: 125° C.
Head temperature: 67°–85° C.
Amount of distillate: 386.0 g
Residue: 340.0 g (catalyst-free)
  Product composition:

|  | Distillate (%) | Residue (%) |
| --- | --- | --- |
| Water | 13.52 | — |
| Methanol | 72.89 | 2.90 |
| Methyl ester | 13.51 | 93.80 |
| 2-hexenoic acid | — | 3.10 |
| Miscellaneous | 0.08 | 0.20 |

The yield of methyl 2-hexenoate is 96.6% of the theoretical value based on the 2-hexenoic acid used.

EXAMPLE 6

Preparation of Adipic Acid Methyl Ester

The reaction is performed and the catalyst separated in the manner described in Example 1.
Acid feed: 219.0 g adipic acid (1.5 mols)
Catalyst: 3.0 g concentrated $H_2SO_4$
Test duration: 6 hours
Methanol added: 64.0 g/hr. (2.0 mols)
Bottom temperature: 125° C.
Head temperature: 67°–88° C.
Amount of distillate: 335.7 g
Residue: 267.3 g (catalyst-free)

|  | Distillate (%) | Residue (%) |
| --- | --- | --- |
| Water | 15.54 | 0.20 |
| Methanol | 83.19 | 4.24 |
| Methyl ester | 1.02 | 93.89 |
| Adipic acid | — | 1.56 |
| Miscellaneous | 0.25 | 0.11 |

Product composition:
The yield of dimethyl adipate is 97.6% of the theoretical value based on the adipic acid used.

EXAMPLE 7

Preparation of Phenylactic Acid Methyl Ester

The reaction is performed and the catalyst separated in the manner described in Example 1.
Acid feed: 408.6 g phenylacetic acid (3.0 mols)
Catalyst: 3.0 g concentrated $H_2SO_4$
Test duration: 6 hours
Methanol added: 64.0 g/hr. (2.0 mols)
Bottom temperature: 125° C.
Head temperature: 67°–89° C.
Amount of distillate: 346.0 g
Residue: 446.6 g (catalyst-free)
  Product Composition:

|  | Distillate (%) | Residue (%) |
| --- | --- | --- |
| Water | 15.20 | 0.25 |
| Methanol | 78.64 | 3.68 |
| Methyl ester | 5.67 | 95.90 |
| Phenylacetic acid | 0.20 | 0.10 |
| Miscellaneous | 0.29 | 0.17 |

The yield of phenylacetic acid methylester is 99.4% of the theoretical value based on the phenylacetic acid used.

EXAMPLE 8

Preparation of Benzoic Acid Methyl Ester

The reaction is performed and the catalyst separated in the manner described in Example 1.
Acid feed: 366.5 g benzoic acid (3.0 mols)
Catalyst: 3.0 g concentrated $H_2SO_4$
Test duration: 6 hours
Methanol added: 64.0 g/hr. (2.0 mols)
Bottom temperature: 125° C.
Head temperature: 69°–81° C.
Amount of distillate: 355.4 g
Residue: 395.0 g (catalyst-free)
  Product composition:

|  | Distillate (%) | Residue (%) |
| --- | --- | --- |
| Water | 14.67 | 0.21 |
| Methanol | 78.74 | 2.51 |
| Methyl ester | 6.43 | 95.61 |
| Benzoic acid | 0.02 | 1.59 |
| Miscellaenous | 0.14 | 0.08 |

The yield of methyl benzoate is 98.0% of the theoretical value based on the benzoic acid used.

EXAMPLE 9

Preparation of 2-Ethylhexanoic Acid Methyl Ester

The reaction is performed and the catalyst separated in the manner described in Example 1.
Acid feed: 432.6 g 2-ethylhexanoic acid (3 mols)
Catalyst: 3.0 g concentrated $H_2SO_4$
Test duration: 6 hours
Methanol added: 64.0 g/hr. (2.0 mols)
Bottom temperature: 125° C.
Head temperature: 67°–84° C.
Amount of distillate: 415.5 g
Residue: 400.3 g (catalyst-free)
Product composition:

|  | Distillate (%) | Residue (%) |
|---|---|---|
| Water | 12.42 | 0.18 |
| Methanol | 67.50 | 2.59 |
| Methyl ester | 18.50 | 95.65 |
| 2-Ethylhexanoic acid | 1.22 | 1.28 |
| Miscellaneous | 0.37 | 0.30 |

The yield of the methyl ester of 2-ethylhexanoic acid is 96.9% of the theoretical value based on the 2-ethylhexanoic acid used.

What we claim is:

1. A process for the preparation of methyl carboxylate comprising reacting a saturated or unsaturated, straight or branched chain, mono or dicarboxylic acid having more than 5 carbon atoms with a molar excess of methanol over said acid in the presence of an acid catalyst taken from the class consisting of mono and multibasic, non volatile, inorganic and organic acids and acid salts at a temperature of 100° to 150° C. and below the boiling point of said carboxylate.

2. The process of claim 1 wherein said methanol is added to a mixture of said acid and said catalyst.

3. The process of claim 1 wherein there are 1 to 6 mols of said methanol per equivalent of said acid.

4. The process of claim 1 wherein said catalyst is concentrated sulfuric acid.

5. The process of claim 1 wherein said temperature id 110° to 130° C.

6. The process of claim 5 wherein said temperature is 115° to 125° C.

7. The process of claim 1 wherein 1 to 6 mols of methanol per equivalent of acid are present.

8. The process of claim 1 wherein 2.0 to 5.0 mols of methanol per equivalent of acid are present.

9. The process of claim 8 wherein 3.0 to 4.0 mols of methanol per equivalent of acid are present.

10. The process of claim 4 wherein said catalyst is 0.1 to 3 grams of concentrated sulfuric acid per mol of said carboxylic acid.

11. The process of claim 1 wherein said catalyst is 0.5 to 1.5 grams of concentrated sulfuric acid per mol of said carboxylic acid.

12. The process of claim 1 wherein said acid is taken from the class consisting of heptanoic acid, dipropylacetic acid, 2-ethylhexanoic acid, cyclohexanoic acid, 2-hexenoic acid, adipic acid, phenylacetic acid, benzoic acid, and mixtures thereof.

13. The process of claim 1 wherein said catalyst is taken from the class consisting of sulfuric acid, phosphoric acid, methane sulfonic acid, ethane sulfonic acid, chlorosulfonic acid, p-toluene sulfonic acid, sodium hydrogen sulfate, and mixtures thereof.

* * * * *